United States Patent [19]

Brodsky et al.

[11] Patent Number: 5,139,018

[45] Date of Patent: Aug. 18, 1992

[54] PATIENT VENTILATING APPARATUS WITH ASPIRATING CATHETER

[75] Inventors: David L. Brodsky, Providence; Harry O. Olsen, Warwick, both of R.I.

[73] Assignee: Superior Healthcare Group, Inc., Cumberland, R.I.

[21] Appl. No.: 737,422

[22] Filed: Jul. 11, 1991

Related U.S. Application Data

[63] Continuation-in-part of Ser. No. 557,190, Jul. 24, 1990, abandoned.

[51] Int. Cl.⁵ .............................................. A61M 16/00
[52] U.S. Cl. .......................... 128/207.14; 128/207.16; 128/912
[58] Field of Search .................. 128/200.26, 207.14, 128/207.15, 207.16, 912

[56] References Cited

U.S. PATENT DOCUMENTS

| Re. 33,219 | 5/1990 | Daniell et al. | 251/7 |
|---|---|---|---|
| 48,421 | 6/1865 | Matthews, Jr. | 251/7 |
| 2,471,623 | 5/1949 | Hubbell | 251/7 |
| 3,213,882 | 10/1965 | Beatty | 251/7 |
| 3,248,011 | 4/1966 | Brodsky et al. | 251/7 |
| 4,351,328 | 9/1982 | Bodai | 128/207.14 |
| 4,488,548 | 12/1984 | Agdanowski | 128/207.15 |
| 4,638,539 | 1/1987 | Palmer | 128/207.16 |
| 4,850,350 | 7/1989 | Jackson | 128/207.16 |

Primary Examiner—J. Reed Fisher
Assistant Examiner—Aaron J. Lewis
Attorney, Agent, or Firm—Salter, Michaelson & Benson

[57] ABSTRACT

A patient ventilating and aspirating apparatus includes a connector fitting assembly, an elongated tubular flexible aspirating catheter element having a lumen therein, a collapsible sleeve and a closure mechanism which is operative for closing off the lumen in the catheter element. The connector fitting assembly is connectable to a tracheostomy connector installed in a patient and to a respiratory apparatus. The aspirating catheter element is received in the connector fitting assembly, and the collapsible sleeve is sealingly connected to the connector fitting assembly and to the catheter element. The aspirating catheter element is connectable to a source of vacuum, and it is longitudinally slidable in the connector fitting assembly for advancing the catheter element into the trachea of the patient. The closure mechanism is operable for controlling the application of vacuum to the catheter element without promoting residue build-ups therein by selectively collapsing the catheter element to close off the lumen therein. The apparatus preferably further includes an irrigation port for irrigating the lumen in the catheter element in order to avoid clogging the catheter element.

11 Claims, 5 Drawing Sheets

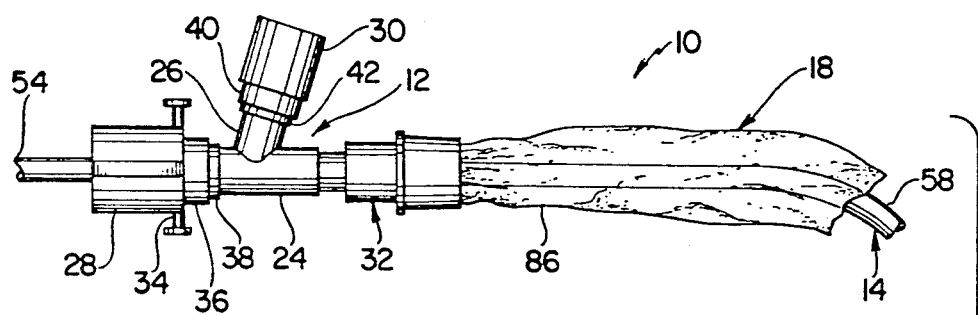
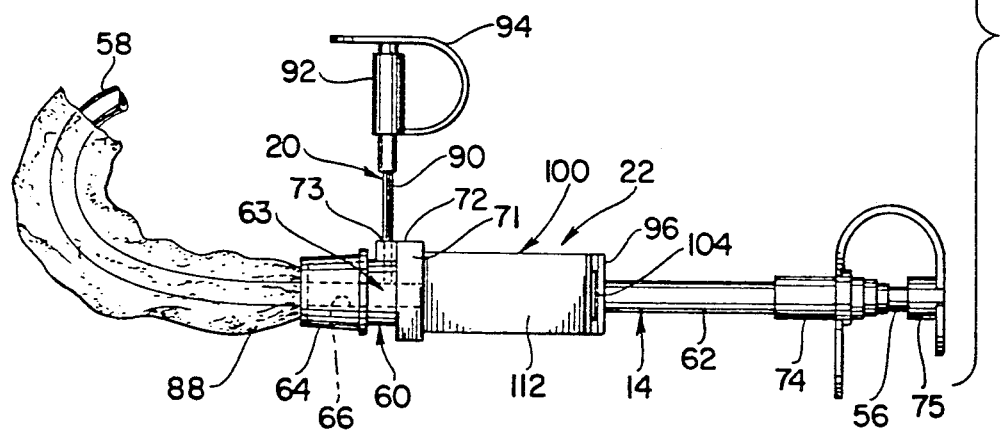
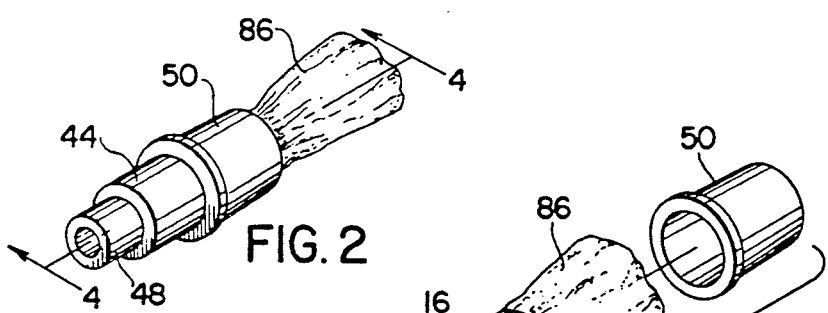
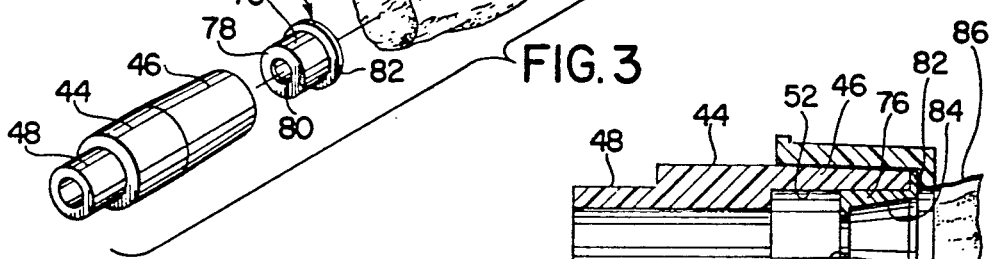
FIG. 1
FIG. 2
FIG. 3
FIG. 4

PATIENT VENTILATING APPARATUS WITH ASPIRATING CATHETER

BACKGROUND AND SUMMARY OF THE INVENTION

This application is a continuation-In-Part of Ser. No. 07/557,190, filed July 24, 1990, now abandoned.

The instant invention relates to medical apparatus and more particularly to an apparatus for ventilating the respiratory system of a patient and for aspirating fluids from within the trachea and/or bronchi of the patient.

A variety of apparatus have been heretofore available for supplying air to and withdrawing air from the lungs of tracheostomy patients. Many of these devices have also been adapted for aspirating fluids, such as mucus and the like from the trachea of patients during patient ventilation. The heretofore available patient ventilating and aspirating devices of this type have generally comprised connector fittings which are adapted to be connected to tracheostomy connectors installed in the trachea of patients and also to air supplies for involuntarily supplying air to and withdrawing air from the lungs of patients. Devices of this type have generally further comprised aspirating catheters having distal and proximal ends and control means adjacent the proximal ends of the catheters thereof for controlling the levels of vacuum applied thereto. The aspirating catheters of devices of this type have generally been slideably but sealingly received in the connector fittings thereof so that the distal ends of the catheters can be advanced into the trachea of patients. Devices of this type have generally further comprised tubular collapsible outer sleeves which extend around the catheter elements thereof and between the connector fittings and the control means thereof to enable the catheter elements to be manipulated by attending physicians or technicians without causing the hands of the manipulators to come in contact with the catheter elements. Devices of this general type which represent the closest prior art to the subject invention of which the applicant is aware are disclosed in the U.S. Pat. Nos. to Dryden, No. 3,902,500; Radford, No. 3,991,762; and Palmer, No. 4,696,296. However, since the devices disclosed in these references fail to suggest the unique closure means of the apparatus of the subject invention as well as several of the other more specific structural features thereof, they are believed to be of only general interest. Other related devices which are believed to be of still more general interest with respect to the subject invention are disclosed in the U.S. Pat. Nos. to Podhora, No. 3,215,141; Waldman, Jr., No. 3,335,723; Bennet et al, No. 3,825,001; Moorehead, No. 4,068,659; Alley, No. 4,326,520; Frankhouser, No. 4,327,723; Hampson, No. 4,327,735; Muto, No. 4,392,853; Osborne, No. 4,551,137; Gustavsson et al, No. 4,563,176; Bodicky, No. 4,613,329; Taniguchi, No. 4,622,033; Osborne, No. 4,634,433; and Brooks, No. 4,767,409.

While several of the previously known patient ventilating apparatus have included aspirating catheters and control means for controlling the levels of vacuum applied to the aspirating catheters thereof, it has been found that the control means of many of the previously available devices of this type are highly prone to clogging. Specifically, it has been found that control means which include moveable closure valve elements are generally highly prone to clogging because they inherently provide irregularly shaped restricted areas where residual quantities of dried or partially dried aspirated fluids such as mucus, etc. can readily accumulate.

The instant invention provides an improved patient ventilating and aspirating apparatus which can be effectively manipulated by an operator for aspirating fluids from the trachea of a patient without exposing the operator to the fluids which are aspirated from the patient and which is also not prone to clogging as a result of residue buildups in the aspirating portion of the apparatus. More specifically, the ventilating and aspirating apparatus of the instant invention comprises a tubular connector fitting assembly which is connectable to a supply of air and to the trachea of a patient for involuntarily supplying air to and withdrawing air from the lungs of the patient and an elongated flexible tubular aspirating catheter element having a longitudinally extending lumen therein and having distal and proximal ends. The catheter element is sealingly received in the connector fitting assembly so that it is longitudinally slidable therethrough for advancing the distal end of the catheter element into the trachea of a patient. The ventilating and aspirating apparatus further comprises an elongated collapsible tubular sleeve having distal and proximal ends and closure means which is operative for resiliently collapsing the catheter element in order to close off the lumen therein. The distal end of the tubular sleeve is sealingly connected to the connector fitting and the proximal end of the sleeve is sealingly connected to the catheter element, and accordingly, the catheter element can be manipulated through the sleeve for advancing the catheter element into the trachea of a patient without requiring the hands of the operator to contact the surface of the catheter element. The closure means is preferably normally biased to a closed position, and it is preferably operative for collapsing the catheter element at a predetermined location in the longitudinal extent thereof which is between the proximal end of the sleeve and the proximal end of the catheter element. The apparatus preferably further comprises a closable irrigation port which is connectable to a supply of irrigating fluid for supplying irrigating fluid to the interior lumen of the catheter element at a location which is between the proximal end of the sleeve and the closure means. The closure means preferably comprises a cylinder member having an interior chamber therein, and a piston element which travels in the chamber in the cylinder member. The cylinder member includes a pair of opposite side passages which open into the interior chamber therein, and the piston element has a transversely extending passage therethrough. The piston element is received in the cylinder member so that it is movable between an aligned position wherein the passage in the piston element is aligned with the side passages in the cylinder member and a non-aligned position wherein the passage in the piston element is in non-aligned relation with the side passages in the cylinder member. Accordingly, when the closure means is assembled on the collapsible portion of the catheter element it is operative in the aligned position thereof for permitting fluids to flow through the catheter element, and it is operative in the non-aligned position thereof for collapsing the catheter element in order to close off the lumen therein. The closure means preferably further includes a biasing spring for biasing the piston element toward the non-aligned position thereof and guide means for non-rotatably guiding the piston element as it travels in the cylinder member. Still further, the cylinder member preferably has a slightly reduced opening at one end thereof, and the piston element preferably has a button formed at one end thereof which normally projects outwardly through the slightly reduced opening in the end of the cylinder member so that the piston element can be manually manipulatable for moving the piston element between the aligned and non-aligned positions thereof.

It has been found that the apparatus of the instant invention can be effectively utilized for ventilating and aspirating a tracheostomy patient. Specifically, it has been found that the connector fitting assembly can be effectively utilized for supplying air to and withdrawing air from the trachea of a patient in a conventional manner and that the catheter element can be manipulated through the tubular sleeve for advancing the distal end of the catheter element into the trachea of the patient in a conventional manner. However, it has been further found that because the closure means is operative for collapsing the wall of a flexible portion of the catheter element to close off the lumen therein, the closure means is operative without becoming clogged due to residue buildups. In this regard, because the closure means is operative for collapsing the catheter element in order to close off the lumen therein, the interior of the catheter element can be constructed in a substantially smooth and continuous configuration and it is less prone to clogging. Further, because the closure means preferably includes an irrigation port, any residual fluids remaining in the lumen in the catheter element after an aspirating procedure can be flushed out with an irrigating fluid before clogging can occur. Still further, when the closure means is embodied so as to include a cylinder member and a piston element in the cylinder member, the closure means can be constructed so that it can easily fit in a hand of an operator for easy and convenient manipulation thereof by the operator.

Accordingly, it is a primary object of the instant invention to provide an effective and practical apparatus for ventilating and aspirating the respiratory system of a patient.

Another object of the instant invention is to provide a ventilating and aspirating apparatus comprising an aspirating catheter and closure means for the aspirating catheter which is not prone to clogging.

An even still further object of the instant invention is to provide an apparatus for ventilating and aspirating a patient which comprises a suction catheter element and a closure device which is operative for collapsing the suction catheter element in order to close off a lumen therein.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a fragmentary side elevational view of a first embodiment of the ventilating and aspirating apparatus of the subject invention;

FIG. 2 is a perspective view of a portion of the connector fitting thereof;

FIG. 3 is an exploded perspective view thereof;

FIG. 4 is a sectional view taken along line 4—4 in FIG. 2;

DESCRIPTION OF THE INVENTION

Figure 5:
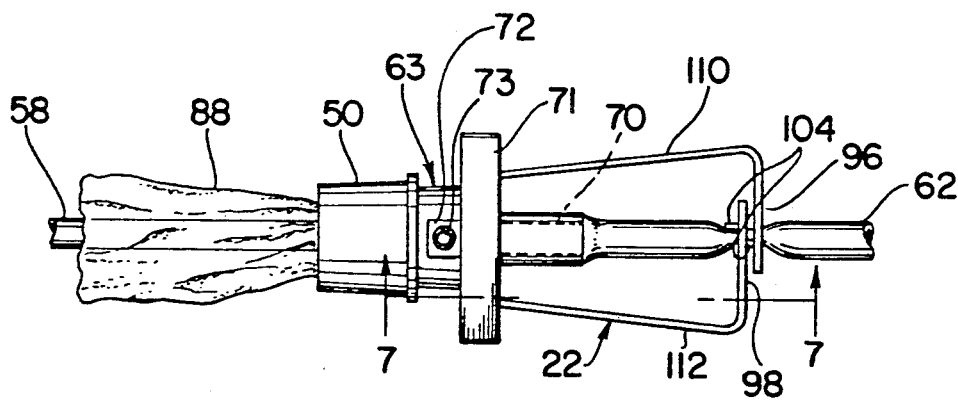
FIG. 5 is a fragmentary top plan view of the proximal end portion thereof with the closure mechanism in a closed position.
Figure 6:
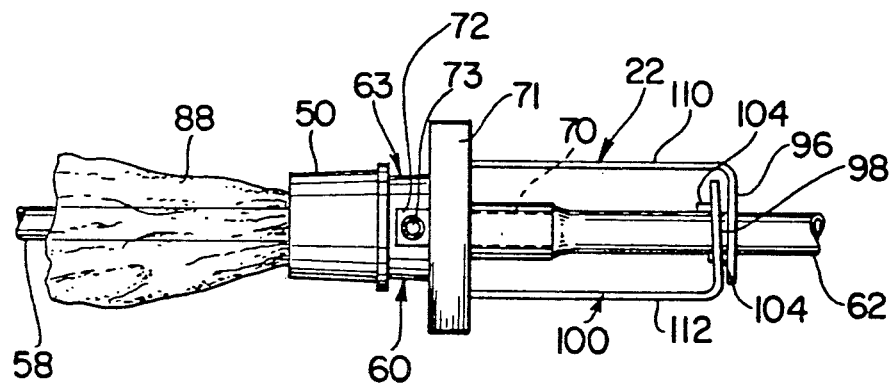
FIG. 6 is a similar view with the closure mechanism in an open position.
Figure 7:
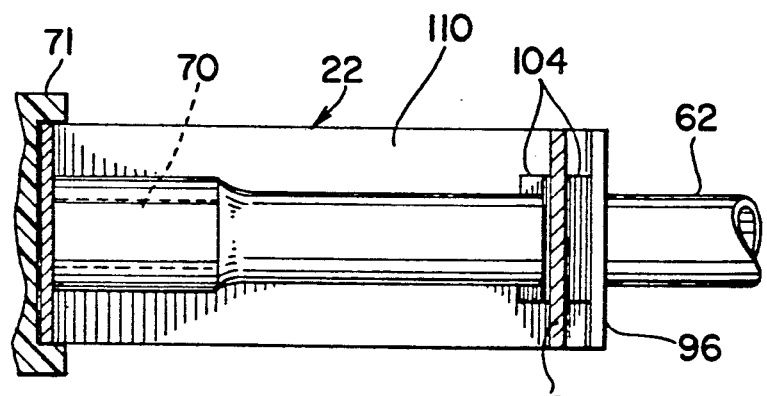
FIG. 7 is an enlarged sectional view taken along line 7—7 in FIG. 5.
Figure 8:
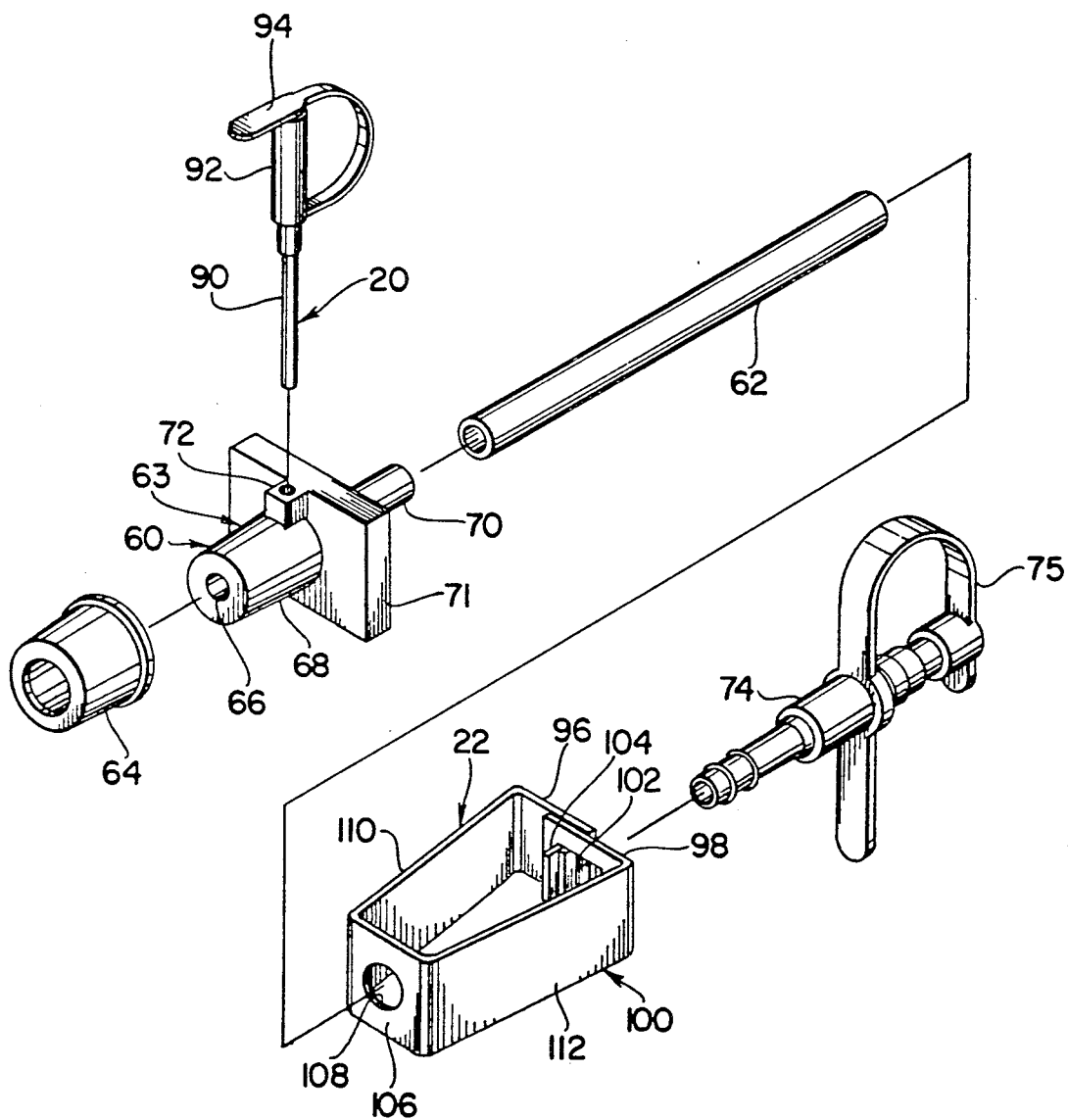
FIG. 8 is an exploded perspective view of the proximal end portion thereof.
Figure 9:
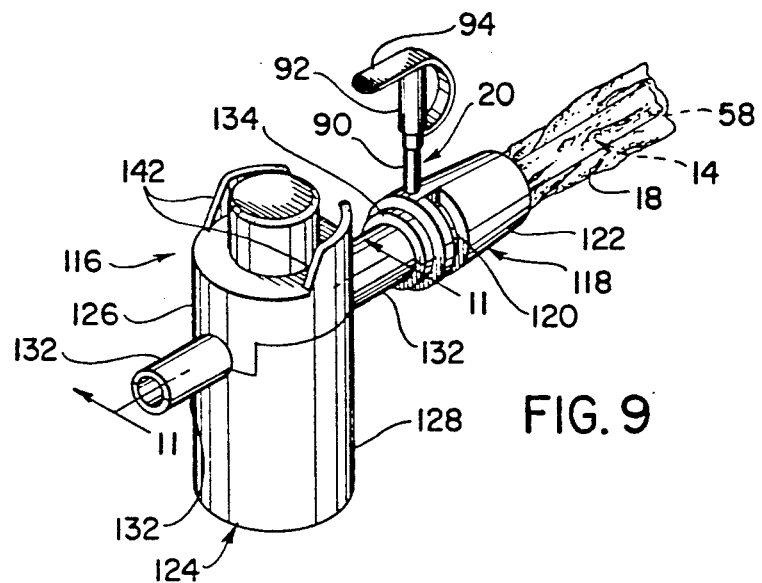
FIG. 9 is a perspective view of the proximal end portion of a second embodiment of the apparatus with the closure mechanism thereof in a closed position.
Figure 10:
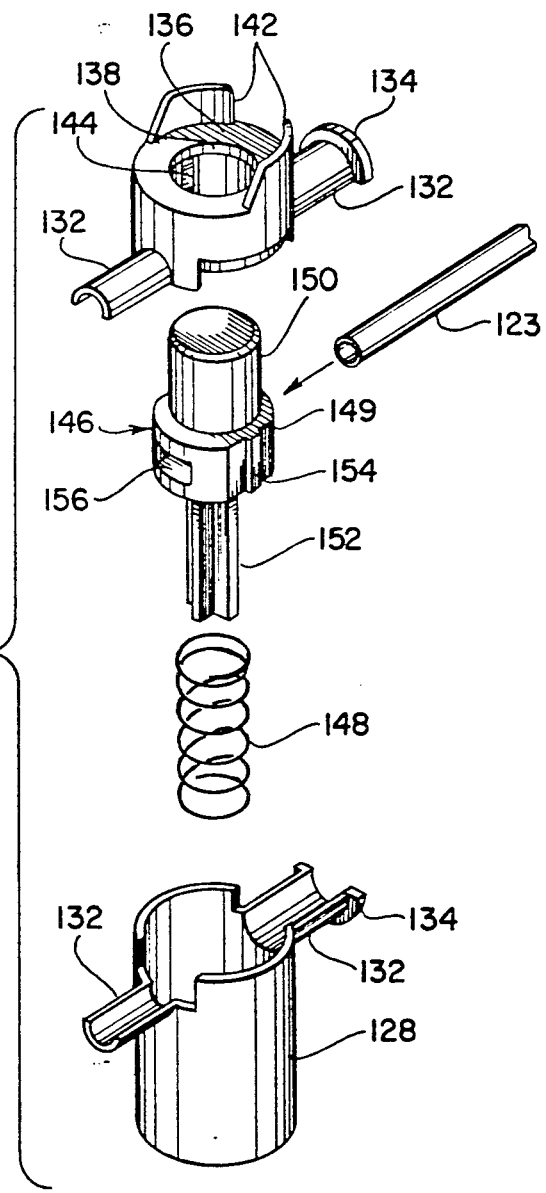
FIG. 10 is an exploded perspective view thereof.

Referring now to the drawings, a first embodiment of the ventilating and aspirating apparatus of the instant invention is illustrated in FIGS. 1-7 and generally indicated at 10 in FIG. 1. The ventilating and aspirating apparatus 10 comprises a connector fitting portion generally indicated at 12, an elongated tubular flexible aspirating catheter assembly generally indicated at 14, a catheter seal generally indicated at 16, an elongated collapsible tubular sleeve 18, an irrigating assembly generally indicated at 20 and a closure mechanism generally indicated at 22. The connector fitting assembly 12 is of conventional construction, and it is adapted to be connected to the trachea of a patient by means of a conventional tracheostomy connector (not shown) which has been surgically installed in the throat of the patient. The catheter element 14 is adapted to be connected to a vacuum source and it is assembled so that it is slidably receivable through the connector fitting assembly 12. The seal 16 is operative for effecting a seal between the connector fitting assembly 12 and the catheter assembly 14 in a manner which allows the catheter assembly 14 to be longitudinally advanced and retracted through the connector fitting assembly 12. The collapsible tubular sleeve 18 is of elongated tubular configuration and it is sealingly connected to the connector fitting assembly 12 and to the catheter assembly 14 in a manner which permits the catheter assembly 14 to be manipulated from the exterior of the sleeve 18 in order to longitudinally advance and retract the catheter assembly 14 through the connector fitting assembly 12. The irrigation assembly 20 is operative for passing an irrigating fluid into the interior lumen of the catheter assembly 14 and the closure mechanism 22 is operative for mechanically closing off the interior lumen of the catheter assembly 14 in order to selectively control the application of vacuum to the catheter assembly 14.

The connector fitting assembly 12 is illustrated in FIGS. 1-4 and it includes a tubular central main section 24, a tubular side ventilating section 26, a main connector element 28 on the main section 24, a side ventilating connector element 30 on the side ventilating section 26 and a sleeve attachment assembly 32. The main and side ventilating sections 24 and 26, respectively, are integrally formed from a suitable plastic material and the main and side ventilating connector elements 28 and 30, respectively, are rotatably attached to the main and side ventilating sections 24 and 26, respectively. The main connector element 28 is of generally tubular configuration and it includes a pair of lugs 34 which extend outwardly from diametrically opposite sides of the connector element 28 for securing the connector element 28 to a conventional tracheostomy connector. The connector element 28 further includes a reduced collar portion 36 which is received on the main section 24 between a pair of annular rings 38 for rotatably securing the main connector element 28 to the main section 24. The side ventilating connector element 30 similarly includes a collar 40 which is received between a pair of annular rings 42 on the side ventilating section 26 for rotatably securing the side ventilating connector element 30 on the side section 26. The sleeve attachment assembly 32 is illustrated most clearly in FIGS. 2-4 and it includes a tubular male fitting 44 having a tapered end portion 46 and a reduced end portion 48, and a female collar 50. The reduced end portion 48 is received and adhesively secured in the tubular main section 24. The tapered end portion 46 has an enlarged axially extending bore 52 therein for receiving the seal element 16 in a manner which will hereinafter be more fully set forth and the female collar 50 is receivable over the tapered end portion 46 for capturing the distal end portion of the sleeve 18 between the tapered portion 46 and the collar 50 and also for retaining the seal 16 in assembled relation in the bore 52.

The catheter assembly 14 has distal and proximal ends 54 and 56, respectively, and it includes an elongated flexible tubular catheter element 58, a sleeve connector portion generally indicated at 60, and a collapsible portion 62 which cooperate to define a single continuous elongated lumen which extends between the proximal end 56 and the distal end 54. The flexible tubular element 58 is of conventional construction and it is preferably made from a suitable flexible elastomeric material, such as a silicone rubber. The sleeve connector portion 60 is preferably molded from a suitable rigid plastic material and it includes a main element generally indicated at 63 and a female collar 64. The main element 63 has a tubular passage 66 therethrough and the flexible catheter element 58 is received in the tubular passage 66 so that the passage 66 provides an extension of the lumen in the flexible catheter element 58. The main element 63 comprises a tapered male section 68, and a reduced tubular section 70 and the passage 66 extends through both the male and tubular sections 68 and 70, respectively. Further included in the main element 63 is an outwardly extending rectangular flange portion 71 which is located at the intersection between the male section 68 and the tubular section 70. An irrigation port 72 having a tubular passage 73 therethrough extends outwardly from the tapered male section 68 so that the passage 73 communicates with the longitudinal passage 66. The female collar 64 is adapted to be snugly received over the male section 68 for securing the tubular sleeve 18 so that it is captured between the female collar 64 and the male section 68 as will hereinafter be more fully set forth. The collapsible section 62 comprises a section of conventional flexible tubing made from a suitable elastomeric material, such as a silicone rubber. The collapsible section 62 is received and secured on the tubular portion 70 so that the interior lumen in the collapsible section 62 extends directly from the interior passage 66 in the main section 63. The collapsible section 62 is constructed so that the wall thereof is collapsible to close off the interior lumen therein by applying clamping pressure to the exterior surface of the collapsible section 62. A conventional tubular fitting 74 is received on the end of the collapsible section 62 and defines the proximal end 56 of the catheter assembly 14, the fitting 74 including a conventional stopper section 75 and being adapted to be connected to a suitable vacuum source in a conventional manner.

The seal 16 is preferably constructed from a suitable resilient elastomeric material, such as a silicone rubber, and it includes a tubular main wall 76, an end wall 78 having an aperture 80 therethrough at one end of the main wall 76 and an annular flange 82 at the opposite end of the main wall 76. As illustrated in FIG. 4 the interior of the main wall 76 is defined by an inner surface 84 which defines a passage which is tapered in a direction toward the end wall 78. The aperture 80 is dimensioned for sealingly receiving the flexible catheter element 58 therethrough and the seal 16 is dimensioned to be received in the bore 52 so that the flange 82 is received in engagement with the terminal end of the tapered portion 46. As a result, the seal 16 is effectively operative for providing a sealed connection between the flexible catheter element 58 and the connector fitting assembly 12 while nevertheless allowing the catheter element 58 to be longitudinally advanced and retracted through the connector fitting assembly 12.

The flexible sleeve 18 is preferably made from a suitable collapsible sheet material, such as polyethylene, in a generally tubular configuration, and it includes distal and proximal end portions 86 and 88, respectively. The distal end portion 86 is received and adhesively secured in the collar 50, and it is also adhesively secured to the tapered end portion 46 so that the distal end portion 86 is effectively captured between the collar 50 and the tapered end portion 46 as illustrated most clearly in FIG. 4. The proximal end portion 88 is similarly adhesively secured in the collar 64 and adhesively secured to the tapered end portion 68 so that the distal end portion 88 is effectively captured and adhesively secured between the collar 64 and the tapered end portion 68.

The irrigating assembly 20 comprises a reduced tubular element 90 which is received in the irrigation port 72, and an end fitting 92 having a stopper element 94. The end fitting 92 is adapted for receiving an irrigating fluid therein in a conventional manner in order to pass the irrigating fluid through the tubular element 90 and into the passage 66 in the main element 63 for irrigating the interior of the catheter element 58.

The closure mechanism 22 is illustrated most clearly in FIGS. 5-8 and it includes first and second end walls 96 and 98, respectively, and a resilient frame portion generally indicated at 100 which is operative for biasing the end walls 96 and 98 outwardly in opposite directions. Each of the end walls 96 and 98 has a substantially rectangular aperture 102 therethrough and a lip portion 104 is formed along one of the edges of the aperture 102 in each of the end walls 96 and 98. The lip portions 104 are constructed so that they define substantially flat engaging surfaces which are engageable with the collapsible element 62, and they are positioned so that they engage opposite side surfaces of the collapsible element 62 to close off the lumen therein as the end walls 96 and 98 are moved apart by the resiliency of the frame portion 100. The frame portion 100 is preferably integrally formed with the end walls 96 and 98 from a suitable resilient metal, and it includes a front wall 106 having a central aperture 108 therethrough and a pair of arms 110 and 112 which extend integrally outwardly from opposite side edges of the front wall 106 to the end walls 96 and 98, respectively. The frame portion 100 is formed so that the arms 110 and 112 are operative for biasing the end walls 96 and 98 outwardly and apart for normally applying pressure to the surface of the collapsible section 62 with the lip portions 104 when the closure mechanism is in an at rest position. However, the frame portion 100 is further formed so that by manually squeezing the arms 110 and 112 together, the apertures 102 are moved into positions of substantial alignment in order to remove the pressure from the exterior surface of the collapsible element 62 so that the interior lumen in the catheter element is opened and vacuum is applied to the tubular catheter element 5B.

For use and operation of the apparatus 10, the connector fitting assembly 12 is connected to a tracheostomy connector (not shown), the side ventilating connector element 30 is connected to a conventional ventilating apparatus, and the tubular fitting 74 is connected to a vacuum source. The flexible catheter element 58 can then be manipulated through the collapsible sleeve 18 for advancing the distal end 14 into the trachea of the patient in order to aspirate fluids from the trachea. Further, the closure mechanism 22 is manually operable by squeezing the arms 110 and 112 together for opening the passage in the collapsible element 62 in order to apply vacuum to the catheter element 58. Once the desired aspirating operation has been completed, the catheter element 58 can be withdrawn from the trachea in a similar manner and the closure mechanism 22 can be released to again close off the interior lumen in the collapsible section 62. Whenever the closure mechanism 22 is in a closed position so that vacuum is not communicated to the catheter element 58 the stopper element 94 can be removed from the irrigating assembly 20 and a suitable irrigating fluid can be passed into the interior lumen of the catheter assembly 14 through the irrigating assembly 20. In any event, as the apparatus 10 is operated in this manner, the seal 16 is operative for effecting a seal around the catheter element 58 which prevents air from the connector fitting assembly 12 from inflating the interior of the sleeve 18. The flange 71 is operative for protecting the closure mechanism 22 against inadvertent opening, such as resulting from a patient inadvertently rolling over onto the closure mechanism 22. The closure mechanism 22 is operative for closing off the interior lumen in the catheter assembly 14 but since it is operative by applying clamping pressure to the collapsible section 62, the closure mechanism 22 and the collapsible section 62 can be constructed without irregular or restricted areas which could promote the accumulation of fluid residues in the catheter assembly 14. Accordingly, the catheter assembly 14 is not prone to clogging as a result of residue buildups and it can be effectively utilized for aspirating fluids from the trachea of the patient.

Referring now to the FIGS. 9 through 12, the closure mechanism portion of a second embodiment of the patient ventilating apparatus of the instant invention is illustrated and generally indicated at 116. Closure mechanism 116 is connected to a catheter assembly 14 and to a collapsible sleeve 18 with a sleeve connector portion 118 having an irrigation assembly 20 therein which is adapted so that it communicates with the interior lumen in the catheter assembly 14. The closure mechanism 116 is operative in a manner similar to the closure mechanism 22 for collapsing or closing off the interior lumen in the catheter assembly 14 in order to interrupt the application of vacuum to the distal end portion of the catheter assembly 14.

The sleeve connector portion 118 comprises male and female portions 120 and 122, respectively, and the proximal end portion of the tubular sleeve 18 is captured between the male and female portions 120 and 122, respectively, and ultrasonically secured thereto for securing the sleeve connector portion 118 to the tubular sleeve 18. The catheter assembly 14 passes longitudinally through the sleeve connector portion 118 and a relatively short rigid tube section (not shown), is received in the interior of the catheter element 58 where it passes through the sleeve connector portion 118. The rigid tube section (not shown) and the catheter element 58 are received and secured in one end of the closure mechanism 116 so that the catheter element 58 passes through the closure mechanism 116. In this connection, the catheter element 58 is actually normally constructed so that it is inherently collapsible along substantially the entire length thereof, but in any event, it is essential that at least that portion of the catheter element 58 which passes through the closure mechanism 116 (in this case a collapsible section 123) be collapsible to permit the closure mechanism 116 to operate to close off the lumen therein.

The irrigating assembly 20 is essentially identical to the irrigating assembly 20 illustrated in connection with the apparatus 10, and it includes a reduced tubular element 90 which extends into the interior of the catheter element 58 an end fitting 92 and a stopper element 94. Accordingly, the irrigating assembly 20 is operative for supplying an irrigating fluid to the interior of the catheter element 58.

The closure mechanism 116 comprises a housing generally indicated at 124 which includes upper and lower housing sections 126 and 128, respectively. The housing 124 is of generally cylindrical configuration and the housing sections 126 and 128 cooperate to define an interior chamber 130. Each of the upper and lower housing sections 126 and 128 includes a pair of aligned integrally molded tube section halves 132, and a flange half 134 is integrally molded on one of the tube section halves 132 on each of the upper and lower housing sections 126 and 128, respectively. Accordingly, when the upper and lower housing sections 126 and 128 are received in assembled relation, the tube section halves 132 cooperate to define a pair of substantially aligned tubular passages which extend through opposite side sections of the housing 124, and the flange halves 134 cooperate to define a circular flange at the end of one of the tubular passages, as illustrated. The upper housing section 126 includes a top wall 136 having a central opening 138 therein, and the lower housing section 128 includes a bottom wall 140. Also included in the upper housing section 126 is a pair of side wall extensions 142 which extend upwardly beyond the end wall 136, and a pair of longitudinally extending guide tracks 144 is formed in the interior of the upper housing section 126.

Figure 11:
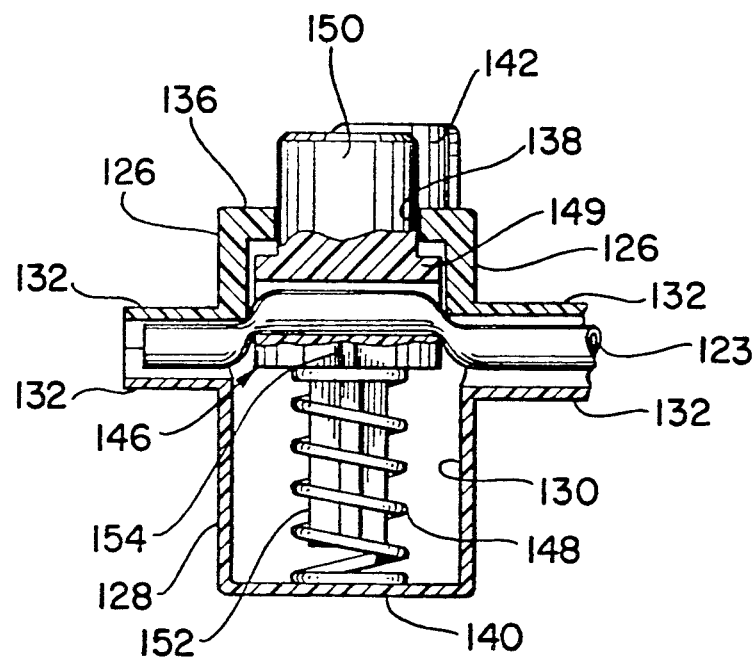
FIG. 11 is a sectional view taken along line 11—11 in FIG. 9.
Figure 12:
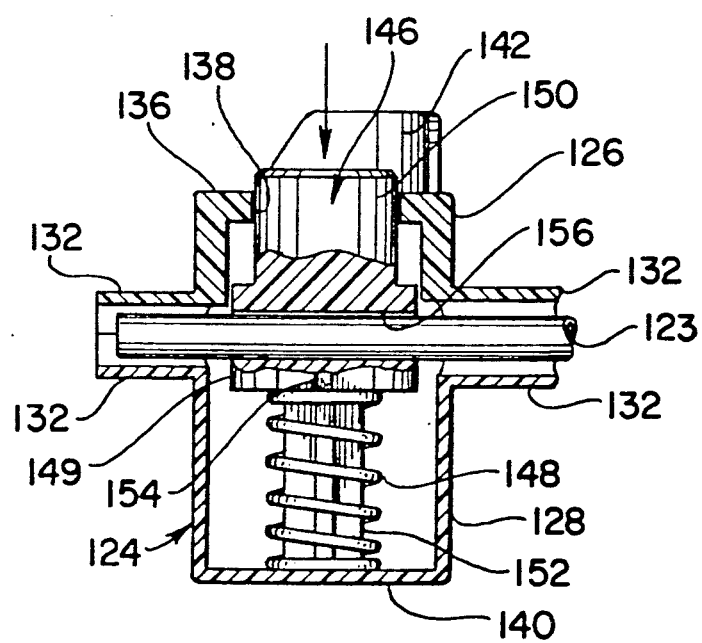
FIG. 12 is a similar view with the closure mechanism thereof in an open position.

The closure mechanism 116 further includes a piston element generally indicated at 146 and a biasing spring 148. The piston element 146 includes an enlarged main portion 149, a slightly reduced upper button portion 150 and a lower end portion 152. The main portion 149 is dimensioned to be slidably received in the upper housing section 126, and it includes longitudinally extending ridges 154 on opposite sides thereof which are receivable in the guide tracks 144 in the upper housing section 126 for guiding the longitudinal travel of the piston element 146 in the housing 124. The enlarged main portion 149 further includes a transversely extending open passage 156 which is dimensioned for receiving the collapsible portion 123 of the catheter element 58 there-through. As illustrated in FIG. 12, the passage 156 is oriented so that the piston element 146 is longitudinally movable in the housing 124 with the ridges 154 travelling in the tracks 144 for aligning the passage 156 with the tubular passages defined by the tube section halves 132. As illustrated in FIG. 11, the piston element 146 is further adapted so that it is longitudinally movable in the housing 124 to a non-aligned position wherein the passage 156 is in upwardly offset non-aligned relation with respect to the tubular passages defined by the tube section halves 132. The lower end portion 152 of the piston element 146 is formed in a reduced cross-sectional dimension so that the biasing spring 148, which comprises a conventional coil spring, is receivable on the lower end portion 152, as illustrated in FIGS. 11 and 12. Further, as illustrated in FIGS. 11 and 12, the biasing spring 148 is adapted so that it is operative for biasing the piston element 146 to a closed position wherein the passage 156 is in upwardly offset non-aligned relation with respect to the passages in the tube section halves 132.

Accordingly, during normal use of the closure mechanism 116, the biasing spring 148 is operative for biasing the piston element 146 to the non-aligned closed position illustrated in FIG. 11, wherein the passage 156 is in upwardly offset non-aligned relation with respect to the passages defined by the tube section halves 132. As a result, the piston element 146 is normally operative for collapsing the collapsible section 123 of the catheter element 58 in order to close off the lumen therein. More specifically, when the closure mechanism 116 is in the closed position, the lower wall of the passage 156 is operative for pinching the collapsible section 123 of the catheter element 58 against the cylindrical wall of the upper housing section 126 in order to close off the lumen in the collapsible section 123. However, by manually depressing the button portion 150, the piston element 146 can be moved downwardly into the housing 124 in order to move the passage 156 into aligned relation with the tubular passages defined by the tube section halves 132. As illustrated in FIG. 12, once the button portion 150 has been depressed in this manner the lumen passing through the collapsible section 123 is no longer closed off by the piston element 146 and the housing 124 so that a suction can be applied to the catheter element 58 by means of a suitable vacuum source connected to the closure mechanism 116. Further, during use of an apparatus comprising the closure mechanism 116 the side wall extensions 142 protect the mechanism 116 against inadvertent opening thereof, such as caused by a patient inadvertently rolling onto the closure mechanism 116.

It is seen therefore that the instant invention provides an effective apparatus for ventilating and aspirating a patient. The apparatus of the subject invention is effectively connectable to a conventional ventilating apparatus and to a tracheostomy connector for involuntarily supplying air to and withdrawing air from the lungs of a patient. The catheter assembly 14 can be effectively utilized for aspirating fluids from the trachea of a patient and since both the closure mechanism 22 and the closure mechanism 116 are operative without internal valve components they are substantially less prone to becoming clogged as a result of residue buildups. Further, because of the overall relatively simple constructions of the closure mechanisms 22 and 116, the apparatus of the subject invention is highly reliable and not prone to mechanical malfunctions. Hence, it is seen that the ventilating and aspirating apparatus of the instant invention represents a significant advancement in the medical art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An apparatus for ventilating and aspirating the respiratory system of a tracheostomy patient comprising:
   a. tubular connector means connectable to a supply of air and to the trachea of said patient for involuntarily supplying air to and withdrawing air from the lungs of said patient;
   b. an elongated tubular flexible aspirating catheter element having distal and proximal ends, said catheter element having a suction lumen extending longitudinally there-through, said catheter element being received in said connector means and being longitudinally advanceable there-through for advancing the distal end of said catheter element into the trachea of said patient, said proximal end being connectable to a vacuum source for applying aspirating suction through said distal end, said catheter element including a collapsible portion adjacent said proximal end, said collapsible portion having an exterior surface and being resiliently collapsible by the application of pressure o the exterior surface of said collapsible portion;
   c. seal means for sealing between said catheter element and said connector means while nevertheless allowing said catheter element to be longitudinally advanced and retracted through said connector means;
   d. an elongated collapsible tubular sleeve have distal and proximal ends, the distal end of said sleeve being sealingly connected to said connector means, said catheter element extending longitudinally through said sleeve, and passing sealingly through the proximal end thereof; and
   e. closure means for closing off said lumen, said closure means comprising a cylinder member having at least one open end and an interior chamber therein and having a pair of opposite side passages therein which open into said interior chamber, said collapsible portion passing through said cylinder member so that it extends through said side passages, and a piston element traveling longitudinally in said chamber and having a transversely extending passage there-through, said collapsible portion of said catheter element passing through said transversely extending passage, said piston element being manually movable in said chamber between an aligned position wherein the passage in said piston element is aligned with the side passages in said cylinder member to permit fluid flow through said catheter element, and a non-aligned position wherein the passage in said piston element is in non-aligned relation with said side passages in said cylinder member for collapsing said catheter element in order to close off the lumen therein, said piston element having a button formed at one end thereof, said button being accessible adjacent the open end of said cylinder member and being manually movable from a non-depressed position to a depressed position for manually moving said piston element between the non-aligned and aligned positions thereof, respectively, said cylinder member further comprising at least one sidewall extension extending beyond the open end of said cylinder member along said button when the latter is in the non-depressed position thereof for preventing inadvertent movement of said button toward the depressed position thereof.

2. In the apparatus of claim 1, said closure means further comprising means biasing said piston element toward one of either said aligned position, or said non-aligned position.

3. In the apparatus of claim 1, said closure means further comprising means biasing said piston element toward the non-aligned position thereof.

4. In the apparatus of claim 1, the open end of said cylinder member having a smaller transverse cross-sectional dimension than said chamber, said piston element being captured in said cylinder member so that said button normally projects outwardly through said open end.

5. The apparatus of claim 1, further comprising guide means for non-rotatably guiding the travel of said piston element in said cylinder member.

6. In the apparatus of claim said closure means being operative for closing said collapsible portion at a predetermined location in the longitudinal extent of said collapsible portion which is between the proximal end of said sleeve and the proximal end of said catheter element, said apparatus further comprising closable irrigation means connectable to a supply of irrigation fluid, and communicating with said lumen for supplying said irrigation fluid thereto at a location which is between said predetermined location and the proximal end of said sleeve.

7. A device for closing off a longitudinally extending lumen in a flexible tubular catheter member comprising:
 a. a cylinder member having at least one open end and an interior chamber therein and having a pair of opposite side passages therein which open into said interior chamber for receiving said tubular catheter member therein so that the latter extends through said cylinder member;
 b. a piston element traveling longitudinally in said chamber and having a transversely extending passage there-through for receiving said tubular catheter member therein so that the latter also extends through said piston element, said passage having opposite ends, said piston element being manually movable in said chamber between an aligned position wherein the passage in said piston element is aligned wit the side passages in said cylinder member to permit fluid flow through said tubular catheter member when the latter is received in said clamping device, and a non-aligned position wherein the passage in said piston element is in non-aligned relation with the side passages in said cylinder member for being said tubular catheter member in order to close off the lumen therein when said tubular catheter member is received in said device; and
 c. said piston element having a button formed at one end thereof, said button being accessible adjacent the open end of said cylinder member and being manually movable from a non-depressed position to a depressed position for manually moving said piston element between the non-aligned and aligned positions thereof, respectively, said cylinder member further comprising at least one sidewall extension extending beyond the open end of said cylinder member along said button when the latter is in the non-depressed position thereof for preventing inadvertent movement of said button toward the depressed position thereof.

8. The device of claim 7 further comprising means biasing said piston element toward one of either said aligned position or said non-aligned position.

9. The device of claim 7, further comprising means biasing said piston element board the non-aligned position thereof.

10. In the device of claim 7, the open end of said cylinder member having a smaller transverse cross-sectional dimension than both said chamber and said piston element, said piston element being captured in said cylinder member so that said button normally projects outwardly through said open end.

11. The device of claim 7 further comprising guide means for non-rotatably guiding the travel of said piston element in said cylinder member.

* * * * *